United States Patent [19]

Thiel

[11] 4,352,789

[45] Oct. 5, 1982

[54] AEROSOL COMPOSITIONS CONTAINING FINELY DIVIDED SOLID MATERIALS

[75] Inventor: Charles G. Thiel, Saint Paul, Minn.

[73] Assignee: Minnesota Mining and Manufacturing Company, Saint Paul, Minn.

[21] Appl. No.: 131,030

[22] Filed: Mar. 17, 1980

[51] Int. Cl.³ .............................................. A61K 9/14
[52] U.S. Cl. ....................................... 424/46; 252/10; 252/306; 424/330
[58] Field of Search ........................................... 424/46

[56] References Cited

U.S. PATENT DOCUMENTS

| | | | |
|---|---|---|---|
| 2,597,702 | 5/1952 | Benning | 260/461 |
| 2,868,691 | 1/1959 | Porush et al. | 424/46 |
| 3,014,844 | 12/1961 | Thiel et al. | 424/46 |
| 3,094,547 | 6/1963 | Heine | 260/461 |
| 3,095,355 | 6/1963 | Abramson et al. | |
| 3,169,095 | 2/1965 | Thiel et al. | 424/46 |
| 3,190,799 | 6/1965 | Cohen et al. | 424/46 |
| 3,560,607 | 2/1971 | Hartley | 424/46 |
| 3,970,584 | 7/1976 | Hart et al. | 252/305 |
| 3,970,586 | 7/1976 | Schliebs et al. | 252/355 |

*Primary Examiner*—Leonard Schenkman
*Attorney, Agent, or Firm*—Cruzan Alexander; Donald M. Sell; Jennie G. Boeder

[57] ABSTRACT

An aerosol composition capable of dispensing dry particles uniformly in a very fine particle size, comprising solid particles coated with a dry coating of a perfluorinated surfactant, suspended in a propellant. The propellant utilized may be of the perfluorinated environmentally preferred type.

18 Claims, No Drawings

AEROSOL COMPOSITIONS CONTAINING FINELY DIVIDED SOLID MATERIALS

This invention relates to self-propelling, powder dispensing aerosol compositions and to a means for dispensing a dry powder in aerosol form having controlled, uniformly fine particle size in an improved, uniform distribution pattern. This invention also relates to aerosol compositions which can be utilized with perfluorinated propellants. The invention also relates to a novel method of preparing such improved aerosol compositions.

Various methods are known in the art to dispense powdered material in aerosol form. U.S. Pat. No. 2,868,691 discloses compositions for aerosol administration of medicaments which are prepared by rendering the solid, active medicament soluble in the liquified propellant by means of a polar cosolvent. Unfortunately, as is well recognized in the art (U.S. Pat. No. 3,014,844), many solids, and particularly certain medicaments, are not stable in polar solvents, or they are rendered unstable when in a polar solvent and contacted with a metal valve often used in pressurized aerosol containers. This is the case with epinephrine. Polar solvent-containing systems may also attack and corrode the metal valve closures of the containers and interfere with their functioning. In addition, some medicaments and other solids cannot be satisfactorily solubilized in the usual liquified propellants, even though a cosolvent is employed. Accordingly, it has not been possible to provide a polar solvent-containing system which provides stable suspensions of powder in a liquified propellant for use in aerosol containers.

To avoid the use of polar solvents an alternative system for providing a self-propelling powder-dispensing aerosol composition is disclosed in U.S. Pat. Nos. 3,014,844 and 3,169,095. The solid powder is suspended in a liquified propellant, in which the solid material is substantially insoluble, and a liquid non-ionic non-fluorinated surface-active agent. The nature of the surface-active agent is quite critical for production of an acceptable aerosol composition and it is required that the surface-active agent be soluble or dispersible in the propellant. The propellants utilized are fluorinated or chlorofluorinated lower alkanes. The viscous liquid surfactants of U.S. Pat. No. 3,014,844 and 3,169,095 retard the evaporation of the sprayed propellant. The viscous liquid surfactants also have a tendency to glue the sprayed solid powdered particles together. Both of these effects increase the size of the sprayed aerosol particles.

Thus, the prior art has not provided a stable self-propelling powder-dispensing aerosol system which can disperse powdered material in as fine a spray as the present invention. In addition, the prior art has not disclosed surface-active agents which would be of use in providing a very fine spray of powdered material when utilizing the more environmentally safe perfluorinated propellants.

The self-propelling, powder-dispensing aerosol compositions of the present invention comprise a finely-divided solid material or powder coated with a dry coating of a perfluorinated surface-active dispersing agent and suspended in a halogenated propellant, in which the solid material and the perfluorinated surface-active dispersing agent are substantially insoluble.

The present invention is an advance over the prior art in that it provides aerosol compositions which are capable of dispensing a powdered substrate in a particle size which is finer and more uniform than that provided by aerosol compositions of the prior art. This feature is of prime importance to the area of aerosol compositions for inhalation therapy. Medicaments useful for inhalation therapy must be well dispersed in the propellant vapor. Smaller particle size permits better dispersion of medicament in the propellant vapor and permits more medicament to travel down the throat and into the lungs. In addition, smaller particles of medicament uniformly dispersed in the propellant provide a composition which is more efficiently absorbed in the bronchioles and alveoli than dispersions of medicament having larger particle size.

While we not not wish to be bound by any theory to explain the excellent results which are obtained with the aerosol compositions of the present invention, the ability to deliver the solid material in a smaller particle size than is the case with the prior art is due to the perfluorinated surfactants and the manner in which they are used. We have observed that in general as surfactant concentration increases so does the droplet size of the aerosol particles. Since the practice of the present invention results in very little surfactant being used, the droplet size of the aerosol particles can be kept at a minimum. In addition the surfactants of the present invention utilized as a dry coating on the solid powdered material will not retard propellant evaporation and will not glue the solid particles together. Thus, the present invention can provide aerosol particles having a very small particle size.

In addition the present invention provides an aerosol composition useful with conventional chlorofluorinated propellants as well as perfluorinated propellants to provide fine dispersions of powdered substrates. Perfluorinated propellants are preferred by environmentalists because they are known not to cause adverse environmental effects associated with chlorofluorinated propellants.

The perfluorinated surface-active dispersing agents of the present invention (hereinafter referred to as "perfluorinated surfactants" or "surfactants") are insoluble in the propellant. This insolublity is due to the relatively ionic character of one end of the surfactant molecule. This ionic group is compatible with the solid powdered material and enables the surfactant to wet the solid material. Although the perfluorinated surfactant is insoluble in the propellants, when coated on the solid material, the outermost perfluorinated groups of the surfactant allow the solid coated material to be dispersed in the propellant due to the compatibility between the perfluorinated groups and the propellant.

Perfluorinated surfactants most useful in the compositions of the present invention include perfluorinated alcohol phosphate esters and their salts; perfluorinated sulfonamide alcohol phosphate esters and their salts; perfluorinated alkyl sulfonamide alkylene quaternary ammonium salts; N,N-(carboxyl-substituted lower alkyl) perfluorinated alkyl sulfonamides; and mixtures thereof. By "perfluorinated" it is meant that the surfactant contains at least one perfluorinated alkyl group. Particularly preferred perfluorinated alcohol phosphate esters are the free acids of the diethanolamine salts of mono- and bis(1H,1H,2H,2H-perfluoroalkyl)phosphates. The phosphate salts, available under the tradename "Zonyl RP" from E. I. Dupont de Nemours and Company, Wilmington, Del., are converted to the corresponding free acids by the method described in Examples 9 and 10.

Preferred perfluorinated sulfonamide alcohol phosphate esters are described in U.S. Pat. No. 3,094,547, and have the general formula:

$$[R_fSO_2N(R)R'O]_m\overset{O}{\overset{\|}{P}}OH_{3-m}$$

wherein R is hydrogen or an alkyl group having from 1 to about 12, preferably from 1 to 6, carbon atoms; R' is an alkylene bridging group containing 2 to about 12 carbon atoms, preferably from 2 to 8 carbon atoms; $R_f$ is perfluoroaliphatic $C_nF_{2n+1}$ or perfluorocycloaliphatic $C_nF_{2n-1}$; n is an integer from 1 to 18, preferably from 6 to 12; and m is an integer from 1 to 3.

Although the mono-, di- and triesters are useful, the diester is most readily available commercially. Particularly preferred perfluorinated sulfanomide alcohol phosphate esters and salts of these include perfluoro-n-octyl-N-ethylsulfonamidoethyl phosphate, bis(perfluoro-n-octyl-N-ethylsulfonamidoethyl)phosphate, the ammonium salt of bis(perfluoro-n-octyl-N-ethyl-sulfonamidoethyl)phosphate, bis(perfluorodecyl-N-ethyl sulfonamidoethyl)phosphate and bis(perfluorohexyl-N-ethyl sulfonamidoethyl)phosphate. The above named preferred surfactants are of particular use in medicinal aerosol compositions due to their non-irritating and non-toxic nature.

The particularly preferred perfluorinated alkyl sulfonamide alkylene quaternary ammonium salt for use in the preparation of aerosol medicaments according to the present invention is N,N-dimethyl-N-decyl-N-(perfluoro-n-octylsulfonamidopropyl)ammonium bromide.

A particularly preferred N,N-bis(carboxyl-substituted lower alkyl)perfluorinated alkyl sulfonamide for use with medicaments in aerosol compositions of the present invention is N,N-bis(4-carboxyl-n-butylperfluoro-n-octylsulfonamide.

The perfluorinated surfactant may constitute from about 0.1 to 20%, desirably between about 0.25 and 5%, and preferably, for medicinal purposes, between about 0.25 and 1%, by weight of the solid material to be suspended. However, the minimum amount of perfluorinated surfactant required is dependent upon the concentration of solid material present. For best results, the concentration of perfluorinated surface-active agent is kept at a minimum as it may tend to increase the droplet size of the aerosol particles.

The compositions of the present invention are useful for a wide variety of powder dispersing applications. They are advantageously used to disperse medicaments in aerosol form. The solid substrate to be dispensed may also be a cosmetic substance such as talc, an antiperspirant such as aluminum chlorohydrate and the like, a polishing material such as jeweler's rouge, a dye such as the approved food colorings, a lubricant such as graphite and other finely-divided materials and other useful substances.

When the solid substrate to be dispensed is a medicament it may be an antiallergic, analgesic, bronchodilator, antihistamine, antitussive, anginal preparation, antibotic antiinflammatory, hormone, or sulfonamide, such as, for example, a vasoconstrictive amine or its acid-addition salts, an enzyme, alkaloid, or steroid, and synergetic combinations of these. Exemplary of the medicaments which may be employed are: Isoproterenol [alpha-(isopropylaminomethyl)protocatechuyl alcohol] hydrochloride or sulfate, phenylephrine bitartrate or hydrochloride, phenylpropanolamine, glucagon, adrenochrome, trypsin, epinephrine bitartrate, ephedrine, narcotine, codeine, atropine, heparin, morphine, dihydromorphinone, ergotamine, scopolamine, methapyrilene, cyanocobalamin, terbutaline, rimiterol, salbutamol, beclomethazone, flunisolide, and colchicine. Others are antibiotics, such as neomycin, streptomycin, penicillin, procaine penicillin, tetracycline, chlorotetracycline and hydroxytetracycline; adrenocorticotropic hormone and adrenocortical hormones; such as cortisone, hydrocortisone, hydrocortisone acetate and prednisolone; insulin, antiallergy compounds such as cromolyn sodium, etc.

Presently preferred medicaments for use in the compositions of the invention are isoproterenol sulfate or hydrochloride, epinephrine bitartrate, and phenylephrine bitartrate or hydrochloride.

For pharmaceutical purposes the particle size of the powder should desirably be uniform and not greater than 100 microns diameter, since larger particles may tend to agglomerate, separate from the suspension and may clog the valve or orifice of the container. Preferably the particle size should be less than 25 microns in diameter. Desirably the particle size of the finely-divided solid powder should for physiological reasons be less than 25 microns and preferably less than about 10 microns in diameter. The present invention can provide epinephrine in an aerosol spray having a mass median diameter of between 1.5 and 2.0 microns.

There is no lower limit on particle size except that which is imposed by the use to which the aerosol produced is to be put. Where the powder is a solid medicament, the lower limit of particle size is that which will be readily adsorbed and retained on or in body tissues. When particles of about one-half micron in diameter are administered by inhalation they tend to be exhaled by the patient.

Desirably the finely divided solid materials should be substantially insoluble in both the liquified propellant and the surface-active agent. Finely-divided solid materials which are predominantly polar in nature provide most satisfactory compositions when used with chlorofluorinated propellants. Although, both polar and non-polar solid materials provide satisfactory compositions when used with perfluorinated propellants. If the solid material is substantially soluble in the propellant, the particle size of the aerosolized material when dispensed cannot be controlled. If the particle size of the suspended solid material cannot be regulated and agglomeration takes place, the valve orifice of the aerosol container may clog, rendering the dispensing device inoperative, or if a metering valve is employed, it may be rendered inaccurate. This may lead to inaccurate dosages, which in the case of highly potent medicinals may lead to undesirable results. In addition to increasing the particle size and clogging orifices, agglomeration may make the suspension unstable, an obviously undesirable result particularly in the case of aerosolized medicinals.

The finely-divided solid material may constitute up to about 20% by weight of the total composition. Desirably it shall constitute up to about 10%, and preferably up to about 3%, by weight of the total composition. The minimum concentration of the solid material is governed by its specific activity and in the case of highly active material can be as low as 0.001% by weight of the total composition although a concentration of 0.01% is preferred.

The halogenated propellant useful in the practice of the invention is one which is a gas at room temperature (25° C.) at atmospheric pressure (760 millimeters of mercury), i.e., it has a boiling point below 25° C. at atmospheric pressure. For use in compositions intended to produce aerosols for medicinal or cosmetic use, the propellant should be essentially non-toxic. Among the most suitable propellants which may be employed are the fluorinated and chlorofluorinated lower alkanes, such as are sold under the trademark "Freon", and certain straight or branched chain or cyclic perfluorinated alkanes, ethers, amines, sulfides and sulfones. Mixtures of the above propellants may be suitably employed.

It is contemplated that the fluorinated or chlorofluorinated lower alkanes shall contain not more than 4 carbon atoms and at least 1 fluorine atom. The preferred lower alkane compounds may be represented generally by the formula $C_mH_nCl_yF_z$, wherein m is an integer equal to or less than 4, n is an integer or zero, y is an integer or zero, and z is an integer, such that $n+y+z=2m+2$. Examples of useful fluorinated propellants include
dichlorodifluoromethane ("Freon 12"),
1,2-dichlorotetrafluoroethane ("Freon 114"),
trichloromonofluoromethane ("Freon 11"),
dichloromonofluoromethane ("Freon 21"),
monochlorodifluoromethane ("Freon 22"),
trichlorotrifluoroethane ("Freon 113"),
trichloromonofluoroethane, monochlorotrifluoromethane ("Freon 13"), chloroheptafluoropropane ("Freon 217") and chloropentafluoroethane ("Freon 115"). Perfluorinated alkanes and cycloalkanes which are useful include perfluoropropane, perfluoro-n-butane, perfluoroisobutane, perfluorocyclopropane and perfluorocyclobutane ("Freon C-318"). Other useful perfluorinated propellants include perfluorodimethyl ether, perfluorodiethyl ether, perfluorofuran, perfluorotrimethylamine, bis(trifluoromethyl)sulfone, bis(trifluoromethyl)sulfide, trifluoromethylpentafluorosulfide and the like.

Presently preferred propellants are selected from three classes, chlorofluorinated lower alkanes, perfluorinated alkanes and straight chain or cyclic perfluorinated ethers. Chlorofluorinated lower alkanes are readily available at low cost. They are safe for use with biological systems, i.e. with medicaments, although they may have a detrimental effect on the environment because they may cause depletion of atmospheric ozone. Perfluorinated alkanes, such as perfluoropropane, are readily available commercially and they have not been cited for potential environmental damage. Straight-chain and cyclic perfluorinated ethers are readily available commercially and possess improved stability relative to chlorofluorinated alkanes. They also are thought to be safer to biological systems than chlorofluorinated alkanes.

The vapor pressure of the propellant system should be at least 13 pounds per square inch gauge (p.s.i.g.) at 70° F. Pressures up to 65 p.s.i.g. at 70° F. may safely be used with metal containers and up to 40 p.s.i.g. at 70° F. with specifically reinforced glass containers. It may frequently be desirable to select a propellant system having a low specific gravity to aid in preparing a satisfactory dispersion of light finely divided powders. Propellants with improved solvating characteristics, specific gravity, and vapor pressure may be obtained by using certain mixtures of compatible propellants.

A particularly preferred propellant mixture for the powdered substrate isoproterenol sulfate is comprised of about 50% perfluoropropane and 50% perfluorofuran. These amounts may be varied by about 10% while retaining excellent propellant characteristics.

In producing the compositions of the present invention a novel and surprisingly effective method is utilized. The active powder ingredient is dispersed in a solution of the perfluorinated surfactant in a solvent in which the powder substrate is substantially insoluble. Suitable solvents are, for example chloroform, dichloromethane, isopropanol, ethanol, and trichlorotrifluoroethane ("Freon 113"). A dispersion of the powder is produced by, for example, homogenization. The dispersed powder is then collected by filtration, decantation, or centrifugation, and subsequently dried. This procedure fosters uniform wetting of the powder particles by the surfactant.

In producing the aerosol packages of the invention a container equipped with a valve is filled with a propellant containing the dried, surfactant-coated powdered material, in suspension. The dried surfactant-coated powder may be dispersed in the cooled liquified propellant by mixing or homogenization. Alternatively, it may be more convenient to homogenize the coated powder in a small quantity of compatible inert fluid to form a concentrated paste which is then dispersed in the propellant. The inert fluid must be soluble in the propellant. Preferred inert fluids are fluorocarbon liquids. Particularly preferred fluorocarbon liquids include perfluorotri-n-butylamine, available under the tradename "FC-47" (medical grade) and "FC-43" (commercial grade) from the 3M Company, St. Paul, Minn., and the perfluorinated dimer of methylcyclopentadiene, available under the tradename "FC-48", from the 3M Company. Propellant is added to the aerosol package by either the cold filling method or by pressure filling through the valve nozzle. On operating the valve of the aerosol container, the powder will be dispensed in a stream of propellant, which will vaporize providing an aerosol of dry powder. Throughout the preparation of the product care is desirably exercised to minimize the absorption of moisture where the powder is water-soluble. This may be accomplished by operating in a dehumidified atmosphere using only dry materials and equipment.

The compositions of the invention may be used to dispense consistently accurate doses of aerosolized solid medicaments into body cavities such as throat or nose. They also provide a means of producing aerosolized medicaments suitable for inhalation therapy. Inhalation therapy enables drugs to act directly on respiratory sites without engendering undesirable systemic effects as often happens when drugs are administered by other routes. With very volatile substances inhalation approaches intravenous therapy in rapidity of action. The compositions of the present invention are of particular efficacy in inhalation therapy since the very small size of the medicament particles dispersed uniformly in the propellant are more efficiently absorbed in the bronchioles and alveoli than are the larger particles of medicament provided by the aerosol compositions of the prior art. Also, as illustrated by Example 28, less of the medicament provided by the present invention is impacted in the throat and more of the medicament is available for inhalation than is the case with the aerosol formulations of the prior art.

The compositions of the present invention are useful with the more environmentally safe perfluorinated propellants as well as with conventional fluorochlorinated propellants. In contrast, the surfactants of the prior art do not perform well as dispersing agents in perfluorinated propellants.

In order more clearly to disclose the nature of the present invention, the following examples illustrating compositions in accordance with the invention will now be described. It should be understood, however, that this is done solely by way of example and is intended neither to delineate the scope of the invention nor limit the ambit of the appended claims. In the examples which follow, the process described above was employed. In the examples which follow and throughout the specification, the quantities of material are expressed in terms of percentages by weight of the total composition, unless otherwise specified. The range of particle size specified is that existing at the time of formulation. Where a constituent is described as "micronized," it comprises 90% by weight of particles having a particle size range of between 1 and 5 microns.

EXAMPLE 1

A mixture of 1.0 g of micronized epinephrine bitartrate and 0.5 g of a perfluorinated sulfonamide alcohol phosphate ester surfactant, sold under the tradename "FC-161" by the 3M Company, St. Paul, Minn. and comprising over 90% perfluoro-n-octyl-N-ethyl sulfonamidoethyl phosphate, was dispersed mechanically in 50 g of isopropanol. After one to two minutes of mechanical agitation the mixture was allowed to settle for five minutes. The mixture was filtered and the solid surfactant-coated drug collected was dried in a vacuum oven at 58° C. for thirty minutes.

A sample of the dried solid (0.5 g) was put into a chilled glass bottle and 49.75 g of "Freon 114" and 49.75 g of "Freon 12" were added and mixed to provide an aerosol formulation of:

|   | Percent |
| --- | --- |
| Surfactant-coated epinephrine bitartrate | 0.5% |
| Freon 114 (50%), Freon 12 (50%) | q.s. |

The contents of the bottle were used to fill aerosol vials and the vials were sealed with metering valves.

EXAMPLE 2

A solution of 300 mg of the ammonium salt of bis(perfluoro-n-octyl-N-ethylsulfonamidoethyl)phosphate was partially solubilized by means of a Virtis Homogenizer (available from the Virtis Co., Inc., Gardiner, NY) in 60 ml of isopropanol. Undissolved surfactant was removed by filtration. 49 G. of the surfactant filtrate was used to disperse one gram of micronized epinephrine bitartrate by homogenization. The epinephrine solid was separated and dried. The dried powder was used to prepare an aerosol formulation in "Freon 114" and "Freon 12" according to the procedure of Example 1.

EXAMPLES 3–8

In the following table (Table I) several surfactant solutions and corresponding aerosol formulations are set forth.

Surfactant solutions were prepared by dissolving the surfactant in a solvent. 5 G of micronized epinephrine bitartrate was coated with the surfactant by homogenization in 50 ml of surfactant solution. After homogenization the mixture was filtered and the solid coated epinephrine bitartrate obtained was dried.

Aerosol formulations comprising 0.5% and 1.0% coated epinephrine bitartrate were prepared by homogenizing 1.0 g or 2.0 g of coated drug in 50 ml of "Freon 114" for 2 minutes. Additional "Freon 114" was then added to provide the desired concentration of coated drug. The resultant suspension was transferred to a bottle and "Freon 12" was added. The bottle was capped and shaken. The propellant composition of the aerosol formulations was 50% "Freon 114" and 50% "Freon 12".

TABLE I

| Example | Surfactant Solution | Amt. Coated Drug in Aerosol Formulation (% by wt.) |
| --- | --- | --- |
| 3 | 1% "FC-161" in isopropanol | 0.5% |
| 4 | | 1.0% |
| 5 | 0.5% bis(perfluoro-n-octyl-N-ethyl sulfonamidoethyl)phosphate in isopropanol | 0.5% |
| 6 | | 1.0% |
| 7 | 0.5% "Zonyl RP"[1] in "Freon 113" | 0.5% |
| 8 | | 1.0% |

[1]"Zonyl RP" is a fluorinated surfactant sold by DuPont Co., Wilmington, Delaware, and comprises diethanolamine salts of mono- and bis(1H,1H,2H,2H-perfluoroalkyl)-phosphates where the alkyl group is even-numbered in the range $C_4$-$C_{18}$ and the fluorine content of the salts is 52.4% to 54.4% as determined on a solids basis.

The aerosol suspensions of Examples 3–8 had differing flocculation characteristics. The aerosol formulations containing 1% coated drug settled more rapidly than those containing 0.5% coated drug. The amount of surfactant-coated drug which coated the walls of the aerosol bottle increased in the following order:

Examples 3 and 4 > Examples 5 and 6 > Examples 7 and 8.

EXAMPLES 9 AND 10

"Zonyl RP" obtained commercially from DuPont Co., Wilmington, Del., was converted to the purified free acid by acidification with hydrochloric acid followed by extraction of the desired product into diethyl ether. Surfactant solutions of 0.5% by weight dried extracted "Zonyl RP" in "Freon 113" were prepared.

Micronized epinephrine bitartrate was coated with surfactant by homogenizing a 5 g sample in 50 ml of surfactant solution. After homogenization, the mixture was filtered and the solid epinephrine bitartrate was dried.

Aerosol suspensions of 0.5% by weight coated drug and 1% by weight coated drug were made up, as in Examples 7 and 8, by homogenizing 1.0 or 2.0 g samples of the coated drug in 50 ml of "Freon 114", adding "Freon 114" to obtain 101 and 102 g of suspension respectively, and then adding "Freon 12" to provide 201 and 202 g of solution, respectively.

When compared with the aerosol suspensions of Examples 7 and 8, the suspensions of Examples 9 and 10 showed reduced tendency to flocculate.

EXAMPLE 11

To 100 ml of chloroform 0.5 g of the surfactant bis(-perfluoro-n-octyl-N-ethylsulfonamidoethyl)phosphate was added. Into this mixture five grams of micronized isoproterenol sulfate was dispersed by homogenization. The powder was separated by filtration and dried. A 100 mg sample of this powder was then dispersed in 200 mg of liquid perfluorotri-n-butylamine by mixing in a milling apparatus for one minute. A 100 mg portion of this dispersion was transferred to a plastic-coated glass aerosol vial. The mixture was placed in a deep-freeze apparatus and liquid perfluoropropane was added. The vial was sealed with a 50 microliter valve.

The resultant aerosol formulation was:

|  | Percent |
|---|---|
| Surfactant-coated isoproterenol sulfate powder | 0.33 |
| Perfluorotri-n-butylamine | 0.67 |
| Perfluoropropane | 99.0 |

EXAMPLE 12

A surfactant solution of 0.5% "Zonyl RP" (purified and converted to the free acid according to the procedures of Examples 9 and 10) in "Freon 113" was prepared by dissolving "Zonyl RP" in the solvent.

Micronized isoproterenol sulfate was coated with surfactant by homogenizing a 5 g sample in 50 ml of surfactant solution. After homogenization, the mixture was filtered and the solid coated isoproterenol sulfate was dried.

An aerosol suspension was prepared by homogenizing 0.30 g of coated drug in 50 ml of "Freon 114" for 2 minutes, adding more "Freon 114" to provide 80.3 g of mixture and then adding "Freon 115" to provide 200.3 g of mixture.

The aerosol formulation was:

|  | Percent |
|---|---|
| Surfactant-coated isoproterenol sulfate | 0.15 |
| "Freon 114" | 39.94 |
| "Freon 115" | 59.91 |

EXAMPLE 13

A surfactant solution of 0.5% by weight "Zonyl RP" in "Freon 113" was prepared, as in Example 12.

A mixture of micronized isoproterenol hydrochloride (0.572 g) and micronized phenylephrine bitartrate (0.858 g) was coated with surfactant by homogenization in surfactant solution, followed by filtration, and drying of the solid coated drug.

An aerosol suspension was prepared by homogenizing the solid coated drug (1.43 g) in 50 ml of "Freon 114" adding more "Freon 114" to provide 81.43 g of mixture and then adding "Freon 115" to provide 201.4 g of mixture.

The aerosol formulation was:

|  | Percent |
|---|---|
| Surfactant-coated drug | 0.71 |
| "Freon 114" | 39.72 |
| "Freon 115" | 59.57 |

EXAMPLE 14

A surfactant solution of 1.0% bis(perfluoro-n-octyl-N-ethylsulfonamidoethyl)phosphate in "FC-113" was prepared, as in Example 11.

A mixture of micronized isoproterenol hydrochloride (0.572 g) and micronized phenylephrine bitartrate (0.858 g) was coated with surfactant according to the procedure of Example 13.

An aerosol suspension of the coated solid mixture in "Freon 114" and "Freon 115" was prepared according to the procedure of Example 13.

EXAMPLES 15-17

Aerosol suspensions were prepared according to the procedures of Examples 12-14, using twice the concentration of surfactant-coated drug.

EXAMPLE 18

A mixture of 3.0 g of micronized epinephrine bitartrate, 0.60 g of bis(perfluoro-n-octyl-N-ethylsulfonamidoethyl)phosphate and 30 ml of "Freon 113" was homogenized for 2 minutes. The mixture was filtered and the surfactant-coated drug was dried. A paste was prepared by mixing the coated drug with three times its weight of "FC-48". A vial was rinsed with "Freon 11", air dried and 196 mg of the paste was added to the vial. The vial was sealed with a rubber septum and 12 ml of a propellant mixture of 75% "Freon C-318" and 25% "Freon 22" was added by means of a pressure syringe. The resultant aerosol formulation was:

|  | Percent |
|---|---|
| Surfactant-coated epinephrine bitartrate | 0.291 |
| FC-48 | 0.873 |
| "Freon C-318" 75%, "Freon 22" 25% | q.s. |

EXAMPLE 19

A solution of 1% bis(perfluoro-n-octyl-N-ethylsulfonamidoethyl)phosphate in "Freon 113" was prepared. A 3 g sample of epinephrine bitartrate was homogenized in 30 ml of the above surfactant solution. The dispersion was filtered and dried to provide surfactant-coated drug.

According to the procedure of Example 18 a paste was prepared of the surfactant-coated drug and "FC-48" and this paste was transferred to a vial after which the propellant mixture was added. The resultant aerosol formulation was:

|  | Percent |
|---|---|
| Surfactant-coated epinephrine bitartrate | 0.291 |
| "FC-48" | 0.873 |
| "Freon C-318" 75%, "Freon 22" 25% | q.s. |

EXAMPLES 20-22

Aerosol formulations were prepared according to the procedure of Example 19 utilizing micronized phenylephrine hydrochloride, micronized isoproterenol hydrochloride and micronized phenylephrine bitartrate as the solid particulate active drug.

EXAMPLE 23

A 0.5% surfactant solution of N,N-dimethyl-N-decyl-N-(perfluoro-n-octylsulfonamidopropyl)ammonium bromide in a solvent mixture of 80% chloroform and 20% isopropanol was prepared. A mixture of 3 grams of micronized isoproterenol sulfate and 30 ml of this surfactant solution was homogenized at high speed in a Virtis homogenizer for one minute. The solid drug was collected by filtration and dried at 60° C. under vacuum for one hour. A paste was prepared by mixing together 100 mg of surfactant-coated drug with 300 mg of "FC-48". A 197 mg portion of the paste was placed in a container and about 10 ml of perfluoropropane was added. The resulting aerosol formulation was:

|  | Percent |
| --- | --- |
| Surfactant coated isoproterenol sulfate | 0.291 |
| "FC-48" | 0.873 |
| perfluoropropane | q.s. |

EXAMPLE 24

A 0.5% surfactant solution of N,N-bis(4-carboxyl-n-butyl)perfluoro-n-octylsulfonamide in a solvent mixture of 80% chloroform and 20% isopropanol was prepared. A mixture of 3 grams of micronized isoproterenol sulfate and 30 ml of this surfactant solution was homogenized at high speed in a Virtis homogenizer for one minute. The solid drug was collected and dried as in Example 23. A paste was prepared by mixing together 100 mg of surfactant-coated drug with 300 mg of "FC-48". A 197 mg portion of the paste was placed in a container and about 10 ml of perfluoropropane was added. The resulting aerosol formulation was:

|  | Percent |
| --- | --- |
| Surfactant coated isoproterenol sulfate | 0.291 |
| "FC-48" | 0.873 |
| perfluoropropane | q.s. |

EXAMPLE 25

A solution of 1.8 g of bis(perfluoro-n-octyl-N-ethyl sulfonamidoethyl)phosphate and 0.20 g of bis(perfluorodecyl-N-ethyl sulfonamidoethyl)phosphate in 100 ml of "Freon 113" was prepared. A mixture of 3 g of micronized isoproterenol sulfate and 30 ml of the above surfactant solution was homogenized. The mixture was filtered and dried to provide surfactant-coated drug. A paste was prepared by mixing 100 mg of the coated drug with 300 mg of "FC-48". 197 Mg of the paste was placed in a container and about 10 ml of perfluoropropane was added. The resultant aerosol formulation was:

|  | Percent |
| --- | --- |
| Isoproterenol sulfate | 0.291 |
| "FC-48" | 0.873 |
| Perfluoropropane | q.s. |

EXAMPLE 26

A solution of 0.025 g of bis(perfluorohexyl-N-ethylsulfonamidoethyl)phosphate, 0.20 g of bis(perfluoro-n-octyl-N-ethylsulfonamidoethyl)phosphate and 0.025 g of bis(perfluorodecyl-N-ethyl sulfonamidoethyl)phosphate in 100 ml of chloroform was prepared. A mixture of 3 g of micronized isoproterenol sulfate and 30 ml of the above surfactant solution was homogenized. The mixture was filtered and dried to provide surfactant-coated drug. A paste was made by mixing the coated drug with three times its volume of "FC-48". 197 Mg of the paste was placed in a container and about 10 ml of perfluoropropane was added. The resultant aerosol formulation was:

|  | Percent |
| --- | --- |
| Surfactant coated isoproterenol sulfate | 0.291 |
| "FC-48" | 0.873 |
| Perfluoropropane | q.s. |

EXAMPLE 27

A solution of 1% bis(perfluoro-n-octyl-N-ethyl sulfonamidoethyl)phosphate and 0.25% "Zonyl RP" in "Freon 113" was prepared.

A mixture of 3 g of micronized epinephrine bitartrate and 30 ml of the above surfactant solution was homogenized. The mixture was filtered and dried to provide surfactant-coated drug. A paste was made by mixing the coated drug with three times its weight of "FC-48". 560 Mg of the paste was placed in a container and about 10 ml of propellant (75% "Freon C-318" and 25% "Freon 22") was added. The resultant aerosol formulation was:

|  | Percent |
| --- | --- |
| Surfactant-coated epinephrine bitartrate | 1.0 |
| "FC-48" | 3.0 |
| "Freon C-318" 75%, "Freon 22" 25% | q.s. |

The foregoing Examples 1–27 illustrate compositions of this invention. Such compositions exhibit a high degree of stability against any tendency of the powdered solid material to agglomerate or to form deposits on the walls of the container.

EXAMPLE 28

The improved smaller particle size of the compositions of the present invention was demonstrated by the use of the "Andersen Sampler" cascade impactor, a device available from the Andersen 2000 Company, Atlanta, Georgia. This machine is widely used for particle size analysis. The following formulations were compared:

1. A commercial aerosol formulation, useful for inhalation therapy, sold under the trademark "Medihaler-Epi" by Riker Laboratories, Inc., Northridge, California, comprising 0.5% by weight epinephrine bitartrate and 1% by weight sorbitan trioleate in a mixture of 25% 1,2-dichlorotetrafluoroethane, 50% dichlorodifluoromethane, and 25% chlorotrifluoromethane.
2. A formulation of epinephrine bitartrate prepared as described in Example 1 in a concentration of 0.5% by weight in a propellant mix comprised of 50% w/w dichlorotetrafluoroethane and 50% w/w of dichlorodifluoromethane.

The formulations were sprayed into a glass "throat" attached to the impactor. The amount of drug impacted in the "throat" was determined in addition to the amount of drug distributed on the stages of the impactor. With the use of the impactor the mass median diameter of the aerosolized drug was determined. Drug impacted in the "throat" is, of course, not available for inhalation. These values are compared below in Table II.

TABLE II

|  | "Medihaler-Epi" | Formulation of Example 1 |
| --- | --- | --- |
| Amount impacted in throat | 58.4% | 39.5% |
| Amount delivered to impactor stages | 41.6% | 60.5% |
| Mass median diameter of delivered aerosol | 2.14 microns | 1.87 microns |

One concludes from the above table that more of the drug is available for delivery to the lungs and more of the drug delivered to the lungs is of an acceptable particle size when the novel aerosol formulation of Example 1 is employed.

What is claimed is:

1. A self-propelling, powder dispensing aerosol composition comprising between about 0.001 and 20 percent by weight of a finely-divided solid material coated with a dry coating of a perfluorinated surface-active dispersing agent which constitutes between about 0.1 to 20 percent by weight of said coated solid material, and suspended in a halogenated propellant in which said solid material and said perfluorinated surface-active dispersing agent are substantially insoluble.

2. A self-propelling, powder dispensing aerosol composition according to claim 1 wherein said finely-divided solid material has a substantially uniform particle size less than about 100 microns in diameter.

3. A self-propelling, powder dispensing aerosol composition according to claim 2 wherein said finely-divided solid material has a substantially uniform particle size of less than about 10 microns in diameter.

4. A self-propelling, powder dispensing aerosol composition according to claim 1 wherein said finely-divided solid material constitutes up to about 3.0 percent by weight of the total composition and said perfluorinated surface-active dispersing agent constitutes between about 0.25 and 1.0 percent by weight of said finely-divided solid material.

5. A self-propelling, powder dispensing aerosol composition according to claim 1 wherein said perfluorinated surface-active dispersing agent is selected from the group consisting of perfluorinated sulfonamide alcohol phosphate esters and their salts; perfluorinated alcohol phosphate esters, their free acids and their salts; perfluorinated alkyl sulfonamide alkylene quaternary ammonium salts; N,N-(carboxyl-substituted lower alkyl) perfluorinated alkyl sulfonamides and their salts; and mixtures thereof.

6. A self-propelling, powder dispensing aerosol composition according to claim 5 wherein said perfluorinated surface-active dispersing agent is a free acid of a perfluorinated alcohol phosphate ester selected from the group consisting of the free acids of mono- and bis-1H,1H,2H,2H-perfluoroalkyl phosphates wherein said alkyl group contains an even number of carbon atoms between 6 and 18, and mixtures thereof.

7. A self-propelling, powder dispensing aerosol composition according to claim 5 wherein said perfluorinated surface-active dispersing agent is selected from the group of perfluorinated sulfonamide alcohol phosphate esters, their salts and mixtures thereof, wherein said ester has the general formula $$[R_fSO_2N(R)R'O]_m\overset{O}{\overset{\|}{P}}OH_{3-m}$$

wherein $R_f$ is a perfluorinated radical selected from the group consisting of aliphatic $C_nF_{2n+1}$ and cycloaliphatic $C_nF_{2n-1}$, n is an integer from 1 to 18, R is selected from the group consisting of hydrogen and an alkyl radical having from 1 to 12 carbon atoms, R' is an alkylene bridging radical having from 2 to 12 carbon atoms and m is an integer from 1 to 3.

8. A self-propelling, powder dispensing aerosol composition according to claim 5 wherein said perfluorinated surface-active dispersing agent is the perfluorinated alkyl sulfonamide alkylene quaternary ammonium salt, N,N-dimethyl-N-decyl-N-(perfluoro-n-octylsulfonamidopropyl)ammonium bromide.

9. A self-propelling, powder dispensing aerosol composition according to claim 5 wherein said perfluorinated surface-active dispersing agent is the N,N-bis(carboxyl-substituted lower alkyl)perfluorinated alkyl sulfonamide, N,N-bis(4-carboxyl-n-butyl)perfluoro-n-octylsulfonamide.

10. A self-propelling, powder dispensing aerosol composition according to claim 7 wherein said surface-active dispersing agent is selected from the group consisting of perfluoro-n-octyl-N-ethylsulfonamidoethylphosphate, bis(perfluoro-n-octyl-N-ethylsulfonamidoethyl)phosphate, the ammonium salt of bis(perfluoro-n-octyl-N-ethylsulfonamidoethyl)phosphate, bis(perfluorodecyl-N-ethyl sulfonamidoethyl)phosphate, bis(-perfluorohexyl-N-ethylsulfonamidoethyl)phosphate, and mixtures thereof.

11. A self-propelling, powder dispensing aerosol composition according to claim 1 wherein said finely-divided solid material is a medicament selected from the group consisting of an antiallergic, an analgesic, a bronchodilator, an antihistamine, an antitussive, an anginal preparation, an antibiotic, an antiinflammatory, a hormone, a sulfonamide and mixtures thereof.

12. A self-propelling, powder dispensing aerosol composition according to claim 11 wherein said medicament is selected from the group consisting of isoproterenol hydrochloride, isoproterenol sulfate, phenylephrine bitartrate, phenylephrine hydrochloride, epinephrine bitartrate and mixtures thereof.

13. A self-propelling, powder dispensing aerosol composition according to claim 1 wherein said halogenated propellant is selected from the group consisting of fluorinated lower alkanes, chlorofluorinated lower alkanes, perfluorinated alkanes, perfluorinated cycloalkanes, perfluorinated ethers, perfluorinated cyclic ethers, perfluorinated amines, perfluorinated cyclic amines, perfluorinated sulfides, perfluorinated cyclic sulfides, perfluorinated sulfones, perfluorinated cyclic sulfones, and mixtures thereof.

14. A self-propelling, powder dispensing aerosol composition according to claim 13 wherein said halogenated propellant is a mixture of about 50% perfluoropropane and 50% perfluorofuran.

15. A self-propelling, powder dispensing pharmaceutical composition capable of providing a medicament in aerosol form suitable for inhalation therapy, comprising a liquified non-toxic propellant, up to 20% by weight of a finely-divided therapeutically active powdered medicament of substantially uniform particle size of less than about 100 microns coated with a dry coating of a perfluorinated surface-active dispersing agent and suspended in said propellant, and between about 0.1 and 20% of the weight of said finely-divided coated medicament being said perfluorinated surface-active dispersing agent; said surface-active dispersing agent and said coated medicament being substantially insoluble in said propellant.

16. A method for preparing an aerosol composition comprising
   (a) coating a finely divided solid material with a perfluorinated surface-active dispersing agent in a solvent in which said finely divided solid material is substantially insoluble,
   (b) separating said coated solid material from said solvent,
   (c) drying sid coated finely divided solid material,
   (d) dispersing said coated solid material in a halogenated propellant in which said solid material and said perfluorinated surface-active agent are substantially insoluble;
such that said aerosol composition comprises between about 0.001 and 20 percent by weight of said solid material and between about 0.1 and 20 percent by weight of said coated solid material is said perfluorinated surface-active dispersing agent.

17. A self-propelling, powder dispensing aerosol composition comprising between about 0.001 and 20 percent by weight of a finely-divided solid material coated with a dry coating of a perfluorinated surface-active dispersing agent which constitutes between about 0.1 to 20 percent by weight of said coated solid material, and suspended in a halogenated propellant in which said solid material and said perfluorinated surface-active dispersing agent are substantially insoluble; said solid material being a medicament, and said perfluorinated surface-active dispersing agent being selected from the group consisting of perfluorinated sulfonamide alcohol phosphate esters and their salts; perfluorinated alcohol phosphate esters, their free acids and their salts, perfluorinated alkyl sulfonamide alkylene quaternary ammonium salts; N,N-(carboxyl-substituted lower alkyl)perfluorinated alkyl sulfonamides and their salts; and mixtures thereof.

18. In an improved aerosol container comprising a pressure-tight container having a valve-controlled opening and containing a pharmaceutical composition, said aerosol container being capable of providing a measured dose of medicament in aerosol form suitable for inhalation therapy; the improvement wherein said pharmaceutical composition comprises the composition of claim 11.

* * * * *